United States Patent
Schuler et al.

(10) Patent No.: US 12,102,513 B2
(45) Date of Patent: Oct. 1, 2024

(54) APPARATUS AND METHOD FOR EQUIPPING TAMPON APPLICATORS WITH TAMPONS

(71) Applicant: Ruggli AG, Koblenz (CH)

(72) Inventors: Samuel Schuler, Basel (CH); Patrick Baumgartner, Tegerfelden (CH)

(73) Assignee: Ruggli AG, Koblenz (CH)

( * ) Notice: Subject to any disclaimer, the term of this patent is extended or adjusted under 35 U.S.C. 154(b) by 466 days.

(21) Appl. No.: 17/274,611

(22) PCT Filed: Aug. 30, 2019

(86) PCT No.: PCT/EP2019/073210
§ 371 (c)(1),
(2) Date: Mar. 9, 2021

(87) PCT Pub. No.: WO2020/052999
PCT Pub. Date: Mar. 19, 2020

(65) Prior Publication Data
US 2022/0047429 A1    Feb. 17, 2022

(30) Foreign Application Priority Data

Sep. 10, 2018 (CH) ..................................... 1069/18

(51) Int. Cl.
*A61F 13/20* (2006.01)
*B65G 47/84* (2006.01)

(52) U.S. Cl.
CPC ........ *A61F 13/2097* (2013.01); *B65G 47/846* (2013.01)

(58) Field of Classification Search
CPC .............. A61F 13/2097; A61F 13/2082; A61F 13/55185; A61F 13/26; A61F 13/385;
(Continued)

(56) References Cited

U.S. PATENT DOCUMENTS 2,624,078 A    1/1953   Winter et al.
3,568,577 A *  3/1971   Voss ..................... A61F 13/2097
                                                         28/120
(Continued)

FOREIGN PATENT DOCUMENTS

DE    41 19 790 A1   12/1992
DE    43 35 195 A1    4/1995
(Continued)

OTHER PUBLICATIONS

International Search Report in PCT/EP2019/073210, mailed Feb. 18, 2020.

*Primary Examiner* — Sarang Afzali
*Assistant Examiner* — Darrell C Ford
(74) *Attorney, Agent, or Firm* — Collard & Roe, P.C.

(57) ABSTRACT

An apparatus for equipping tampon applicators with tampons includes an encircling guide arrangement with an entry point, at which the tampon applicators are fed into the apparatus. The apparatus furthermore includes an exit point, at which equipped tampon applicators are discharged. The apparatus furthermore includes an equipping unit arranged between the entry point and the exit point and designed for equipping tampon applicators with tampons. A multiplicity of guide units which are guided on the guide arrangement serves for transporting the tampon applicators on the guide arrangement. A guide unit conveys tampon applicators on such apparatus, and a method equips tampon applicators with tampons.

15 Claims, 7 Drawing Sheets

(58) Field of Classification Search
CPC ...... B65G 47/846; B65G 49/00; B65G 47/74; A16F 13/263; B23P 19/00; B23P 19/001; B23P 19/002; B23P 19/003; B23P 19/004
See application file for complete search history.

(56) References Cited

U.S. PATENT DOCUMENTS

| | | |
|---|---|---|
| 3,978,979 A | 9/1976 | Mezey |
| 4,321,993 A | 3/1982 | Hinzmann et al. |
| 4,431,104 A | 2/1984 | Orlowski et al. |
| 4,717,027 A | 1/1988 | Laure et al. |
| 5,203,446 A | 4/1993 | Ufland |
| 5,673,784 A | 10/1997 | Karpinsky et al. |
| 5,915,525 A | 6/1999 | Baker et al. |
| 6,347,697 B1 | 2/2002 | Ouellette et al. |
| 6,374,537 B1 | 4/2002 | Van Wingerden et al. |
| 6,629,595 B2 | 10/2003 | Wiese et al. |
| 6,889,817 B2 | 5/2005 | Leisner |
| 8,047,756 B2 | 11/2011 | Tuffs et al. |
| 8,397,905 B1 | 3/2013 | Tritz |
| 8,728,022 B2 | 5/2014 | Tamburin |
| 8,881,888 B2 | 11/2014 | Overley et al. |
| 8,943,658 B2 * | 2/2015 | Seki ............... A61F 13/2097 28/118 |
| 9,540,127 B2 | 1/2017 | Papsdorf |
| 9,731,848 B2 | 8/2017 | Suzuki et al. |
| 10,252,868 B2 | 4/2019 | Aldazabal Badiola |
| 2003/0146071 A1 | 8/2003 | Wiese et al. |

FOREIGN PATENT DOCUMENTS

| | | |
|---|---|---|
| DE | 295 06 230 U1 | 6/1995 |
| EP | 2 335 666 A1 | 6/2011 |
| EP | 2 821 042 A1 | 1/2015 |
| EP | 2 398 437 B1 | 4/2015 |
| EP | 3 064 455 A1 | 9/2016 |
| GB | 1389820 A | 4/1975 |
| JP | S63-37023 A | 2/1988 |
| KR | 101840007 B1 | 3/2018 |
| NL | 9000982 A | 11/1991 |
| WO | 2015/000827 A1 | 1/2015 |

* cited by examiner

APPARATUS AND METHOD FOR EQUIPPING TAMPON APPLICATORS WITH TAMPONS

CROSS REFERENCE TO RELATED APPLICATIONS

This application is the National Stage of PCT/EP2019/073210 filed on Aug. 30, 2019, which claims priority under 35 U.S.C. § 119 of Swiss Application No. 01069/18 filed on Sep. 10, 2018, the disclosure of which is incorporated by reference. The international application under PCT article 21(2) was not published in English.

The present invention relates to an apparatus for equipping tampon applicators with tampons, and to a method for equipping tampon applicators with tampons, in particular on an encircling guide arrangement, all according to the preambles of the independent patent claims. The present invention furthermore relates to a guide unit for transporting tampon applicators on the encircling guide arrangement.

TECHNOLOGICAL BACKGROUND

Tampon applicators are tubular insertion aids, which are normally composed of plastic, for tampons. In the simplest design, they have a sleeve body with a distal opening through which the tampon, after placement into the body orifice, is released. The ejection of the tampon is performed by means of a proximally applied plunger. The pushing of the plunger into the sleeve body presses the tampon contained therein through said distal opening. More refined forms have a rounded distal head end which is equipped with incisions which, as the tampon is pushed out, open in the manner of a flower. Depressions or ribbed portions have also, in the meantime, become standard designs for increasing ease of use. The plunger is often a small tube through which a withdrawal thread of the tampon is led. During use, this is held using a hand, such that it can be safely positioned.

During the equipping of tampon applicators, a tampon must be transferred into a tampon applicator. This may be realized in a variety of ways. Some methods for equipping tampon applicators are based on the principle of a muzzle loader, in the case of which the tampon is guided through the subsequently distal exit opening into the cavity. Methods also exist in which the tampons are fitted through the proximal opening. In the latter case, it is however necessary for the plunger, which during operation serves for ejecting the tampon out of the distal opening, either to be retroactively attached or to be designed such that the tampon can be placed past said plunger or through said plunger into a tampon body.

The present invention is suitable for example for tampons with applicators as presented in EP 3 016 623 A1 or EP 2 398 437 B1.

Most apparatuses and methods for equipping tampon applicators with tampons operate in intermittent fashion. That is to say, it is also the case that one tampon applicator is provided and equipped in one equipping step. For this purpose, the apparatus stops the tampon applicator in a corresponding orientation for a certain period of time. In the case of apparatuses with fast cycle times, this time period can be very short. Nevertheless, the intermittent and discontinuous equipping process is a limiting factor in the rate of production of tampons with tampon applicators. Furthermore, the stop-and-go system with fast cycle times for intermittent equipping leads to increased material wear.

There is therefore a demand for apparatuses and methods for equipping tampon applicators with tampons which permit a high processing rate.

PRESENTATION OF THE INVENTION

It is therefore an object of the present invention to overcome at least one disadvantage of that which is known. In particular, it is sought to provide an apparatus for equipping tampon applicators with tampons, and a corresponding method and guide unit for transporting tampon applicators on a guide arrangement, which satisfies the high demands with regard to continuous equipping of tampon applicators. In particular, it is sought to provide a corresponding apparatus and a method which can not only operate continuously but is also scalable.

Said object has been achieved by means of an apparatus for equipping tampon applicators with tampons, a corresponding method, and a guide unit according to characterizing parts of the independent claims.

One aspect of the present invention relates to an apparatus for equipping tampon applicators with tampons. The apparatus comprises an encircling guide arrangement with an entry point. At this entry point, the tampon applicators are fed into the apparatus. The encircling guide arrangement furthermore has an exit point, at which equipped tampon applicators are discharged. The apparatus furthermore comprises an equipping unit which is arranged between the entry point and the exit point. Said equipping unit is designed to equip tampon applicators with tampons. For the transport of the tampon applicators on the guide arrangement, a multiplicity of guide units is provided which is guided on the guide arrangement.

The apparatus according to the invention permits a continuous feed of tampon applicators to an equipping unit, which is furthermore scalable by means of a number of guide units. Accordingly, it is for example possible for the number of guide units to be configured such that it can select a corresponding optimum between the number of tampon applicators provided at the entry point and the processing rate of the equipping unit.

In a particular embodiment, the equipping unit is of drum-shaped form and has radially arranged tampon receptacles by means of which the tampon is transferred into the tampon applicator and the equipping takes place.

In a particular embodiment, the guide arrangement comprises at least one rail. Said rail may be configured such that guide units guided on the guide arrangement are mounted movably on the guide arrangement by means of the rail.

In a particularly simple embodiment of this refinement, the guide arrangement comprises a rail which is designed as a T-shaped profile and by means of which corresponding counterparts of the guide units are guided on the guide arrangement.

In the context of the present invention, an infeed may be a passive process, in the case of which for example a tampon applicator is transferred into the apparatus, in particular into a guide unit of the apparatus, by an external means, or may be an active process, in the case of which the apparatus, in particular the guide unit, comprises at least one receiving means for receiving the tampon applicator into the apparatus.

Analogously, the discharge may be a passive process, in the case of which a further external element removes the tampon applicator from the apparatus, in particular from a guide unit, or else may be an active process, in the case of which a tampon applicator is actively discharged from the apparatus, in particular from a guide unit.

In a particular embodiment, both the infeed and the discharge may be effected by means of a plunger which discharges the corresponding tampon applicator out of, or introduces said tampon applicator into, the apparatus, in particular guide unit.

In a particular embodiment, the equipping unit is positioned downstream of the entry point in a conveying direction. The equipping unit is particularly preferably arranged so as to comprise a sphere of activity which overlaps at least one region of the encircling guide arrangement.

In a particular embodiment, the guide units are designed as carriages which are mounted so as to be displaceable along the guide arrangement. The carriages may be mounted by means of rollers with a rail of the guide arrangement.

In a particular embodiment, each guide unit is designed for transporting an individual tampon applicator. For this purpose, the guide unit may for example comprise one tampon applicator receptacle which is designed for receiving one tampon applicator.

By means of the transport of the tampon applicators on the guide arrangement by means of guide units designed as carriages, the apparatus can be optimally adapted to the processing rates of the processing stations. For example, one or more buffer regions may be provided which collect a particular number of guide units in order to then feed these as a batch to the next processing step.

In a particular embodiment, the transport on the guide arrangement is performed in circulating fashion. The guide arrangement may describe a closed circuit, with an entry point, at which the tampon applicators in an unequipped state are fed into the apparatus, and an exit point, at which the tampon applicators in an equipped state exit the apparatus. The guide units in this embodiment are arranged to be mounted so as to be displaceable in circulating fashion on the guide arrangement. Said guide units pick up a tampon applicator at the entry point and guide said tampon applicator to the equipping unit, where the tampon applicator is equipped with a tampon, and ultimately to the exit point, where the equipped tampon applicators are discharged.

In one embodiment, the guide arrangement describes a closed path.

In a further particular embodiment, the guide arrangement comprises a rail which describes a closed path. The guide arrangement may have linear sections which issue into curves.

In a particular embodiment, the guide arrangement describes a substantially oval conveying path. Alternatively, the entire guide arrangement may be of circular design.

In a particular embodiment, the guide arrangement comprises at least one processing space with at least one processing unit.

In a further embodiment, said processing space is positioned along a linear portion of the guide arrangement. The processing space may be designed so as to comprise a row of processing units arranged in series. The processing units may be arranged in series such that they can perform success of processing steps on a workpiece. It is particularly preferable for successive processing steps to be performed on the tampon applicator.

In a particular embodiment, the processing space comprises at least one heating element, at least one shaping element and at least one cooling element.

The heating element is preferably designed to warm the tampon applicator. Tampon applicators are commonly manufactured from a thermoplastic material. The heating element is thus particularly preferably designed so as to realize softening of the thermoplastic material of the tampon applicator without said material beginning to melt. The temperature required for this purpose may be dependent on the selected material of the tampon applicator. The heating element is preferably designed so as to be capable of reaching a temperature of approximately 100° C.+/−10 to 20° C. The heating element may also be designed such that only elements that are to be deformed, in particular the distal end of the tampon applicator, are warmed in targeted fashion.

In a further processing unit, which is designed as a shaping element, it is for example possible for an element of the tampon applicator to be processed into a new shape. In practice, this normally means that a tampon-distal end is deformed. Normally, the distal end is designed as a flower-like opening which, during use, allows the tampon to be ejected by virtue of pressure of the plunger being exerted on the proximal end. During the equipping process, said distal end is open in the manner of a flower in order that the tampon can be introduced through the distal end into the tampon applicator. In order to deform the tampon applicator into its final shape, a corresponding mould may be provided in the shaping element, which mould substantially corresponds in terms of shape to the tampon head and exerts pressure on the tampon applicator, which has been prewarmed by means of the heating element, such that said tampon applicator assumes its closed shape at the distal end.

In a subsequent, third processing unit, which is designed as a cooling element, the warmed tampon applicator can be cooled again. In this way, the thermoplastic material is cured in its shape.

The processing units are particularly preferably designed such that they can receive a batch of guide units for simultaneous processing. For example, a processing unit may be designed to simultaneously receive between two and 24, in particular 36, guide units and correspondingly process these, that is to say heat, deform and/or cool these. Alternatively or in addition, the processing units may be designed to allow a continuous inflow of guide units which move along the guide arrangement to be led through the processing space thereof. It is thus for example possible for stepped warming to be performed at the entry of a guide unit into the heating element, at the exit of which, and during the transfer into the deformation element, the desired temperature is attained at which the conveyed tampon applicator can be correspondingly deformed. Corresponding, the cooling by means of the cooling element may also be performed continuously.

In a particular embodiment, a processing unit in the processing space is designed such that it can perform a multiplicity of processing steps. Accordingly, a processing unit can successively perform warming, deformation and cooling on an individual tampon applicator or batch of tampon applicators.

Mixed variants are also possible, in which individual processing units process batches, whereas other process a continuous series of guide units, with corresponding tampon applicators, which are led past. Accordingly, in one embodiment, it is for example possible for the warming by means of the heating element to take place continuously, whereas the deformation is performed by means of the simultaneous deformation of a batch. Accordingly, it is for example possible for the shaping element to be designed to wait until a number of warm tampon applicators with their corresponding guide units has been collected in the shaping element before deformation is performed by means of a deformation tool, which simultaneously deforms all of the tampon applicators that have collected in the shaping element.

In a particular embodiment, each guide unit comprises at least one applicator receptacle for receiving one tampon applicator. It is preferable for each guide unit to comprise exactly one applicator receptacle for receiving one tampon applicator. Alternatively, the guide units may also be designed such that they can receive a multiplicity of tampon applicators. It would also be conceivable for a guide unit to be designed to have two to six, in particular three, applicator receptacles which are designed to receive tampon applicators.

In a particular embodiment, the applicator receptacles are designed such that a tampon applicator is held in positive-fitting and/or force-fitting fashion in the applicator receptacle. For this purpose, the applicator receptacle may for example be designed so as to substantially correspond to the size of the tampon applicator to be received, or to be larger than the diameter of the longitudinal cross section of a tampon applicator to be received but comprise elements which allow a small force to be exerted on the tampon applicator, wherein said tampon applicator is preferably deformed slightly. For example, the applicator receptacle may be equipped with holding means, for example a rubber lining, a ribbed profile or one or a multiplicity of holding bulges which hold the tampon applicator in the applicator receptacle. In particular, the force-fitting holding action may be a friction-fitting holding action.

In the context of the invention, a holding bulge may be understood to mean a protrusion, protuberance or elevation which extends into the applicator receptacle and limits the volume thereof. The holding bulge may also be formed as a stud or projection which, by means of an elastic stress and/or a resetting force, acts on the volume of the applicator receptacle such that a positive-fitting and/or force-fitting holding action is exerted on a tampon applicator situated therein.

It has surprisingly been found that, even with a slight deformation of the tampon applicator, a sufficient holding action is achieved to transport the tampon applicator in the apparatus for equipping tampon applicators along all provided processing stations without the slight deformation having an adverse effect on the quality of the tampon applicator or impairing the equipping of the tampon applicator with the tampon.

In a particular embodiment, the guide units are mounted on the guide arrangement by means of rollers. For example, the rollers may be fitted on the guide unit so as to engage into a T-shaped profile of a rail of the guide arrangement.

The guide unit particularly preferably comprises three rollers. With a system which comprises three rollers, the guide units can be fixed on the guide arrangement and in the process also optimally follow curved profiles. In this example, in the guide unit, two rollers would be arranged on one axial side of the guide arrangement and a counterpart roller would be arranged on the opposite side, the side situated opposite with respect to the longitudinal axis of the guide arrangement.

In a particular embodiment, the guide arrangement comprises an outer radius and an inner radius. If the guide arrangement is of encircling design, then the outer radius describes a larger circumference than the inner radius. The guide units are particularly preferably mounted on the guide arrangement such that two rollers run on the outer radius and one roller runs on the inner radius. In this way, the guide units can also optimally follow the curved profile of the guide arrangement. In a further particular embodiment, the outer radius is, in straight portions of the guide arrangement, parallel to the inner radius, and in the curved regions, the spacing between the inner radius and the outer radius may be configured to be variable. It is thus possible, for example, to ensure smoother rolling over the curves with three rollers.

In an alternative embodiment, the guide unit comprises four rollers, wherein in each case two rollers are formed as roller pairs on opposite radii of the guide unit. The rollers of a roller pair may be configured so as to be fixed with respect to one another, or else may be configured to be spring-loaded with respect to one another. The rollers of a roller pair are preferably configured so as to be rigid with respect to one another but mounted pivotably with respect to a pivot axis on the guide unit. The pivot axis runs preferably parallel to the axis of rotation of the rollers, which are connected to one another by means of a roller lever, and extends perpendicularly through the roller lever. With two roller pairs mounted so as to be pivotable relative to one another in this way, it is for example possible to ensure smoother rolling over the curves.

In a particular embodiment, the guide unit comprises a holding cassette with an applicator receptacle. The holding cassette may be integrally equipped with the guide unit. The holding cassette is however preferably mounted so as to be movable with respect to the guide unit. The applicator receptacle may be designed with the various features mentioned above which are suitable for receiving a tampon applicator and correspondingly holding said tampon applicator in positive-fitting and/or force-fitting fashion. In the simplest embodiment, the applicator receptacle is a recess which extends through the holding cassette, in particular at right angles to the frontal plane of the holding cassette, and which has a diameter which makes physical contact with at least one region of the surface of the tampon applicator, such that, by means of this physical contact, a positive-fitting and/or force-fitting connection is realized between holding cassette and tampon applicator.

The holding cassette is particularly preferably formed as a single piece.

In a particular embodiment, the holding cassette is composed of a material which exhibits little wear under frictional loads. In particular, the holding cassette is composed of a plastic, for example of a nylon plastic.

In a particular embodiment, the guide unit comprises a guide element which comprises engagement means which can be operatively connected to the guide arrangement such that a displaceable mounting of the guide unit on the guide arrangement exists.

In a further preferred embodiment, the holding cassette is mounted movably with respect to the guide element. In this embodiment, the guide unit may be divided substantially into two functional elements. The holding cassette serves for receiving, supporting and onwardly transferring the tampon applicators in the apparatus, whereas the guide element serves for the support and displaceability of the guide unit on the guide arrangement.

In a particular embodiment, the engagement means are rollers, as discussed above. Alternatively, the engagement means may however also be equipped with a slide bearing which can be operatively connected to a corresponding counterpart of the guide arrangement so as to be displaceable along the longitudinal axis of the guide arrangement.

In a particular embodiment, the holding cassette is mounted movably with respect to the guide element such that the holding cassette is spring-loaded with respect to the guide element. For example, a spring element may be arranged between the holding cassette and the guide element such that a resetting force is exerted on the holding cassette.

In a further particular embodiment, the holding cassette is mounted so as to be movable, in such a way that said holding cassette is mounted so as to be movable substantially at right angles with respect to the longitudinal axis of the guide arrangement in the case of an installed guide unit. The movement of the holding cassette thus takes place in this example in a radial direction with respect to a radius of circulation of the guide arrangement. The resetting force of the spring element may be configured such that, on the one hand, a movement of the holding cassette in a radial direction, that is to say a pulling of the holding cassette away from the guide element, is compensated by the resetting force, or, on the other hand, a displacement of the holding cassette in the direction of the guide element would lead to compression of the spring and the resetting force compensates said movement. It is preferable for a resetting region to be left free between the holding cassette and the guide element such that the movement of the holding cassette is permitted. The resetting spring is particularly preferably fitted in this resetting region or adjacent thereto. Instead of a spring, it is also possible for an elastic band with a corresponding elastic plastic to provide the required resetting force.

In a particular embodiment, the guide arrangement comprises, along its circuit path, at least one drive element which is designed to convey at least one guide unit in a conveying direction. For this purpose, the drive element may for example have a driver which can be operatively connected to the guide unit in order that the drive element can move the guide unit on at least a part of the guide arrangement. Alternatively, the guide units are self-driven. This may be made possible for example by means of a drive at one of said rollers.

In a particular embodiment, a multiplicity of drive elements is positioned along the circuit path of the guide arrangement. In particular, driven regions may differ from non-driven regions, such that the guide units are intermittently moved actively in the conveying direction and, at other points in time, move passively in the conveying direction, for example by being pushed by other guide units, or by utilizing gravitational force as a drive in the case of a corresponding geometrical arrangement of the guide arrangement. It is thus possible for example for the guide arrangement to be arranged vertically, such that the encircling guide arrangement has a gradient on which the guide units are pulled downward, and are accelerated, by gravitational force.

In a particular embodiment, a drive element has a multiplicity of drivers in order to simultaneously convey a multiplicity of guide elements in the conveying direction. It is thus possible, for example by means of one driver, for a drive element to drive a batch of guide elements simultaneously.

The drive elements may also be designed so as to themselves impart a circulating action, such that continuous conveyance in a conveying direction is made possible. On the encircling radius, the drive elements may have a row of drivers which, upon making contact, engage a guide unit and move the latter in the conveying direction until said guide unit moves outside the region of influence of the corresponding drive element, whereupon said guide unit would either be conveyed onward by a following drive element or would be fed for particular processing. Here, the drive element may already have picked up further guide units by means of further drivers.

In a particular embodiment, the apparatus according to the invention comprises a controller for synchronization of the drive elements with the corresponding processing units. Through the control of the drive elements and of the processing units, it is for example possible to realize buffering if a backlog could occur during the processing.

In a particularly preferred embodiment, the controller is dynamic and reacts to the speed of the individual elements, that is to say for example of the processing units and of the drive elements. Here, it is for example possible for the speed of individual elements to be dynamically adapted to decelerations or accelerations in the other elements.

In a particularly preferred embodiment, the equipping unit is constructed in the manner of a drum and has a multiplicity of radially arranged equipping drivers, which are each designed for driving one driving projection of the guide units. The equipping driver may for example be a rib or a recess with a profile which can operatively connect to a corresponding counterpart on the guide unit when the guide unit enters the processing region of the equipping unit. The driving projection of the guide unit may likewise be designed as required by the corresponding equipping driver. In the simplest embodiment, the driving projection is a pin which is driven along by a semicircular equipping driver of the equipping unit.

It is thus possible to precisely control the speed of the guide units, which is beneficial for the later sitting of the tampon applicators in the applicator receptacles. A flexible, highly precisely controllable and gentle process for equipping tampon applicators with tampons is thus provided overall.

A further advantage may be realized if the guide units are formed substantially into pieces, that is to say the guide element and the holding cassette are two separate components. The holding cassette is subject to relatively intense wear as a result of the equipping with tampon applicators and owing to the engaging action of the driving projections of the equipping unit. The holding cassette can be easily replaced with little loss of material. Furthermore, the holding cassette can be adapted to the corresponding dimensions of a tampon applicator. For example, tampon applicators for tampons which are used on days between menstruation are of smaller diameter than tampon applicators that have tampons for use during menstruation. Examples of such tampons of relatively small dimensions are described in EP 2 869 802 B1.

In a particular embodiment, the guide arrangement follows, in the region of the equipping station, a radius which runs parallel to the radius of rotation of an equipping region of the equipping station. For example, the guide arrangement may, in this region, deviate from the basically oval basic shape and follow the radius of the equipping unit. For example, the equipping unit may be of substantially circular design with the correspondingly radially arranged processing regions. The guide arrangement may, from a linear region, describe a curve, which then follows a radius, such that the guide arrangement follows the circumference of the equipping unit in this region. A further curve can bring the guide arrangement back into a linear region.

In a particular embodiment, the equipping station comprises a multiplicity of radially arranged limit stop regions for the coaxial alignment of the applicator receptacle of a guide unit with a tampon receptacle of the equipping station, such that a tampon can be transferred from the tampon receptacle into the applicator receptacle along a transfer axis. The coaxial alignment of the applicator receptacle within the meaning of the present invention applies with regard to the longitudinal axis of the applicator receptacle. It is thus for example possible for a holding cassette to be equipped with a recess as applicator receptacle, which recess extends through the entire holding cassette. Said recess has a longitudinal axis which substantially corresponds to the longitudinal axis of a tampon applicator to be received. Said longitudinal axis is brought into a coaxial orientation with respect to the tampon receptacle of an equipping station, such that a tampon can be transferred into a tampon applicator. This may be performed actively for example by means of a plunger.

During operation, for example in the embodiment with the spring-loaded holding cassette, a displacement of the holding cassette in a radial direction can compensate any inaccuracies, or facilitate a corresponding coaxial arrangement.

For example, in a relaxed state, when the holding cassette is being transported on the guide arrangement, the resetting force can act unhindered in a radial direction. If the guide unit with the corresponding holding cassette is then moved into the region of activity of a limit stop region, the holding cassette is subjected to a force counter to the radial force of the resetting force that acts on the holding cassette. The resetting force can, at this point in time, ensure that the holding cassette and the applicator receptacle are oriented correctly in relation to the equipping unit.

With the apparatus according to the invention, it is possible to permit equipping of tampon applicators in a continuous production process of tampons packaged in applicators. The apparatus according to the invention has particular advantages in terms of scalability, and in terms of the modularity of individual constituent parts. For example, it is possible for the equipping to be adapted to the corresponding feed of tampon applicators or to the processing rate of the equipping unit. The high modularity also makes it possible for wearing parts to be individually exchanged particularly inexpensively without the need to replace major constituent parts of the apparatus. By means of the guide units with the holding cassette, particularly precise equipping of the tampon applicators is possible, which meets even high quality demands. Thus, with the apparatus according to the invention, a tampon will fray little to not at all during the equipping process. At the same time, gentle transport of the tampon applicators is ensured, leading to a visually flawless product which achieves high levels of acceptance with users.

A further aspect of the present invention relates to a guide unit for transporting tampon applicators on an encircling guide arrangement, in particular on a guide arrangement as per the apparatus described above. The guide unit comprises an applicator receptacle for receiving a tampon applicator. The applicator receptacle comprises means for holding the tampon applicator in the applicator receptacle in positive-fitting and/or force-fitting fashion. Said applicator receptacle means can be ensured for example by means of the shape of the applicator receptacle or by means of corresponding structures on the applicator receptacle. Examples for the design of the applicator receptacle have already been discussed above. Possible rubber linings, roughenings, spring elements and/or holding bulges are additionally mentioned as variants. A combination of various such means for positive-fitting and/or force-fitting hold of the tampon applicators is also conceivable.

The guide unit according to the invention furthermore comprises a guide element with engagement means for the supported displacement of the guide unit on the encircling guide arrangement. The engagement means are preferably designed such that they can also follow a curved profile of the encircling guide arrangement. The engagement means may be rigid, or they may be mounted so as to be movable with respect to the longitudinal axis of the guide arrangement, for example by having spring elements.

In the simplest embodiment, the engagement means are rollers or a slide bearing. A combination of rollers and slide elements is also conceivable. For example, it is possible for two rollers to engage on one side into a rail of the guide arrangement, whereas, on the other side, a slide bearing provides the counterpressure required for the rollers to be mounted within the rail.

The guide unit according to the invention furthermore comprises at least one driving projection which can operatively connect to an equipping unit and/or to a drive.

In a particular embodiment, the applicator receptacle is mounted displaceably with respect to the guide element. It is preferably mounted so as to be displaceable in a radial direction with respect to the encircling guide arrangement, as stated above, for example.

In a particular embodiment, the guide unit comprises a multiplicity of drivers. Accordingly, the guide unit may, aside from the driving projection which is provided for interacting with the equipping unit, comprise at least one pin which is designed for interacting with a drive element.

In a particular embodiment, the guide unit comprises a holding cassette which is designed for receiving a tampon applicator.

In a particularly preferred embodiment, the applicator receptacle is composed of a recess which is formed in the holding cassette and the cross section of which at right angles to the longitudinal extent of the recess comprises a multiplicity of protuberances and/or indentations. The holding cassette particularly preferably comprises an applicator receptacle which has at least one, preferably one to four, particularly preferably three, holding bulges which extend into the recess of the applicator receptacle such that the holding bulge(s), in the presence of an inserted tampon applicator, lead to positive-fitting and/or force-fitting hold of the tampon applicator in the applicator receptacle.

A further aspect of the present invention relates to a method for equipping tampon applicators with tampons. The method according to the invention is preferably performed using an apparatus discussed in the introduction and using guide units described above. The method comprises substantially a first step of providing a guide unit for transporting tampon applicators on an encircling guide arrangement. In particular embodiment, in this step, a single tampon applicator is conveyed by means of each guide unit on the encircling guide arrangement. The method according to the invention furthermore comprises equipping an applicator receptacle of the guide unit with a tampon applicator at an entry point. For this purpose, it is possible, for example by means of a tampon applicator feed means, for tampon applicators to be pushed by means of a plunger into a recess of a guide unit, such that said tampon applicators are held in these by means of a positive-fitting and/or force-fitting connection during transport. The entry point may for example be designed such that the tampon applicators are transferred to moving guide units. Alternatively, the guide units may be briefly parked at an entry point while they are equipped with the tampon applicators.

In a particular embodiment, an equipping means for equipping the guide units is designed such that it jointly performs the movement of the guide units at least over a partial region of the guide arrangement, such that a transfer of the tampon applicators to the guide units can be performed during the movement.

The method according to the invention furthermore comprises displacing the guide unit on the guide arrangement from the entry point to an equipping unit. This displacement may, as already discussed above, take place passively or actively by means of the guide unit itself. In the simplest embodiment, this displacement may be made possible by means of a drive element, as likewise described.

The method according to the invention furthermore comprises equipping the tampon applicator with a tampon. This equipping may be performed by means of a described equipping unit.

The method according to the invention furthermore comprises displacing the guide unit on the guide arrangement from the equipping unit to an exit point, where the equipped tampon applicator can be discharged. This discharge may, analogously to the situation at the entry point, be performed dynamically, that is to say by means of a discharge unit which substantially follows the movement of the guide unit and in the process performs the discharge, or in a briefly parked state, by virtue of the guide unit being stopped and the equipped tampon applicator being ejected.

In a particular embodiment of the method according to the invention, during the equipping of the tampon applicator with a tampon, the applicator receptacle of the guide unit is guided so as to be oriented, with regard to its longitudinal axis, coaxially with respect to a tampon receptacle of the equipping unit.

In a further embodiment, the equipping unit engages by means of at least one equipping driver on a driver projection of the guide unit and thus guides said guide unit into the transfer position.

In an embodiment according to the invention, all of the above-stated features may be realized in any desired combination unless they are mutually exclusive.

In the following section, the present invention will now be discussed in more detail on the basis of specific figures and exemplary embodiments, without being restricted to these.

A person skilled in the art will gather from these detailed descriptions further advantageous features which may be realized in a refinement of the present invention.

DESCRIPTION OF THE FIGURES

Exemplary embodiment of the invention will be described on the basis of the following figures.

In the figures.

EMBODIMENT OF THE INVENTION

Figure 1:
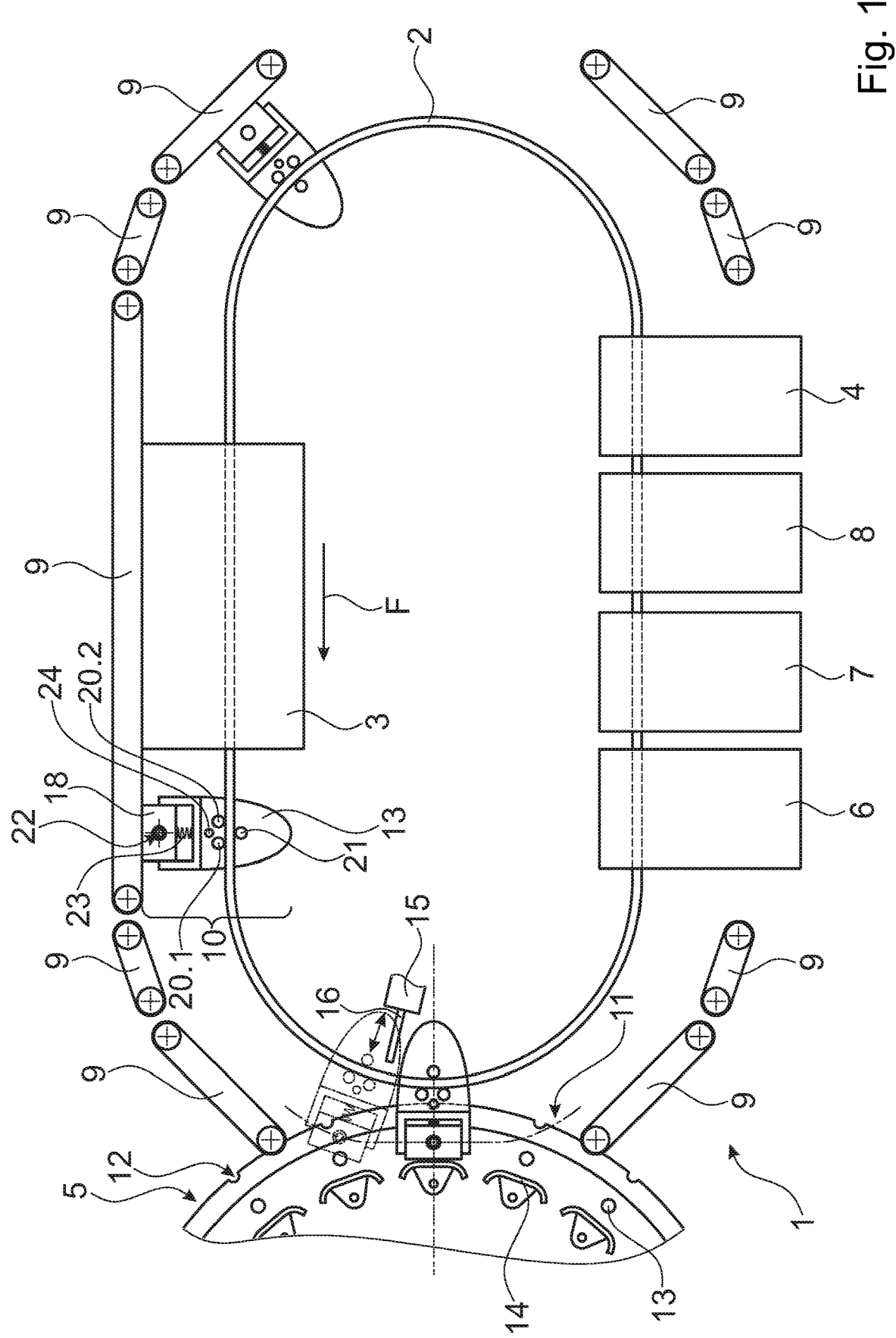
FIG. 1 schematically shows an embodiment of the apparatus according to the invention.

FIG. 1 schematically shows an apparatus 1 for equipping tampon applicators with tampons in one possible realization of the present invention. The apparatus for equipping tampon applicators is organised around an encircling guide arrangement 2. In this example, the guide arrangement 2 is arranged as an elongate rectangle, to narrow sides of which have been replaced by semicircles. The guide arrangement 2 comprises a rail (schematically shown), supported on which a series of guide units 10 can move. In the present example, a total of four guide units 10 are shown for an exemplary illustration.

In one realization of the present invention, it is possible for between four and 4000, in particular between eight and 2000, furthermore in particular between 24 and 400 guide units 10 to be used on one guide arrangement 2 as shown in FIG. 1. The number of guide units 10 may be adapted to the processing rate or the feed of tampon applicators. The guide units 10 serve for transporting individual tampon applicators along the circumference of the guide arrangement 2. Arranged on said circumference of the guide arrangement 2 are various processing stations which can perform a working step on the tampon applicators.

The tampon applicators are introduced at an entry point 3 into an applicator receptacle 22 of a guide unit 10. For this purpose, it is for example possible for a batch of provided tampon applicators to be transferred by means of a plunger into a corresponding number of guide units 10 (not shown). The apparatus 1 discussed in this example has a conveying direction F in which the guide units 10 can be moved into the individual processing stations by means of drive elements 9 or other drive elements which are not shown. For this purpose, the guide units 10 have rollers 20.1, 20.2, 21 which are mounted on the rail of the guide arrangement 2. The guide unit 10 that is shown by way of example close to the entry point 3 has a first roller 20.1 and a second roller 20.2, which are mounted on the outer circumference of the guide arrangement 2, and a counterpart roller 21, which is mounted in the inner circumference of the guide arrangement 2. For this purpose, the guide arrangement 2 may have a rail which is designed as a T-shaped profile and into which the rollers 20.1, 20.2, 21 can engage. The guide arrangement may furthermore, over its circumference, describe variable radii for the outer radius and the inner radius; for example, parallel sections on the straight parts may transition into variable radii at the curves in order to permit improved rolling of the guide units over the curves.

The rollers are arranged in rotatably mounted fashion on a guide element 19. In the present example, said guide element 19 is rigid with respect to the guide arrangement 2. Alternatively, the guide element 19 may be mounted movably with respect to the guide arrangement 2 by means of spring-loaded rollers 20.1, 20.2, 21. Spring-loaded rollers would, by means of a resetting force, be movable in a substantially normal direction with respect to the guide arrangement 2. In the present context, a normal direction is to be understood to mean a direction perpendicular to the tangent of the guide arrangement. In the present, rigid example, the guide element 19 is connected to a spring-loaded holding cassette 18 which comprises the applicator receptacle 22. A resetting spring 23 between the holding cassette 18 and the guide element 19 ensures that the holding cassette 18 is mounted movably with respect to a tangent to the guide arrangement 2. In the present example, a total of nine drive elements 9 is shown. The number of drive elements may however be adapted to the geometry of the guide arrangement 2 as required. In the present example, all drive elements are furthermore driven by means of a head drive of a drive roller. The drive elements 9 may also be driven collectively, by being connected for example using drive belts via a shaft. Thus, a single drive motor would suffice to drive a number of drive elements 9 required for implementing the present invention. The drive elements 9 engage the guide units 10 via drivers (not shown in FIG. 1) and move them in the conveying direction F.

At the first narrow side situated downstream in the conveying direction F, the processing region of the equipping unit 5 begins. The equipping unit 5 is only partially shown in FIG. 1 and, overall, is of rotationally symmetrical and drum-shaped form, such that it has radially arranged tampon receptacles 13. If a guide unit 10 passes into the processing space of the equipping unit 5, an equipping driver 12 of the equipping unit 5 causes the guide unit 10 to be driven along and guided over an alignment radius 11, at which the applicator receptacle 22 of the guide unit 10 is aligned substantially concentrically with the tampon receptacle 13 and the equipping can take place. In the presence of the concentric arrangement, a limit stop region 14 of the equipping unit 5 serves to compress the resetting spring 23 which displaces the holding set 18 in the direction of the guide element 19. The alignment is completed by means of the resetting force of the resetting spring 23. As the guide units 10 are driven along, the equipping drivers 12 operatively connect to a driving projection, formed as a pin on the guide element 24.

In order to optimally control the driving of the guide units 10 on the equipping unit 5, the apparatus 1 additionally has a separating unit 15 with a displaceable stopper 16 which can adapt the guide units 10 to the frequency of the equipping unit 5.

Positioned downstream of the equipping unit 5 is a series of processing units 6, 7, 8. By means of drive elements 9, a guide element 10 passes into the processing units 6, 7, 8. This may be performed continuously, or by means of batches of guide units 10, which are collected and transferred by means of a drive into the individual processing units 6, 7, 8. In the present example, the first processing unit is a heating element, in the case of which the tampon applicators are warmed to a temperature of approximately 100 degrees C. and thus become mouldable, which makes it possible for the downstream second processing unit, the shaping element, to deform the distal end of the tampon applicator such that it closes in the manner of a bud around the tampon. The following processing unit is a cooling element 8, which cools the tampon applicator back to a processing temperature of approximately 20° C. and in the process fixes the shaping.

At an exit point 4, the fully equipped tampon applicators are discharged out of the apparatus 1 and are fed for possible further processing for manufacturing or packaging purposes.

In the embodiment shown by way of example, a buffer region 29 may be positioned downstream of the equipping unit 5. Said buffer region 29 may be of passive design, that is to say it may be a region in which the guide units passively collect, or buffering may be performed actively, for example by virtue of one or more stoppers accumulating a certain number of guide units. When a defined number of guide units has collected in the buffer region 29, these can be conveyed onward in batches or in continuous fashion, for example by means of a driver. This may be performed in batches or by means of individual drivers for the conveying units. In the present example, a buffer region 29 is provided which is positioned downstream of the equipping unit 5 but upstream of the first processing unit 6 of the series of processing units 6, 7, 8, such that, at said buffer region, a number of guide units can be collected and transferred in batches to the processing unit.

Figure 2:
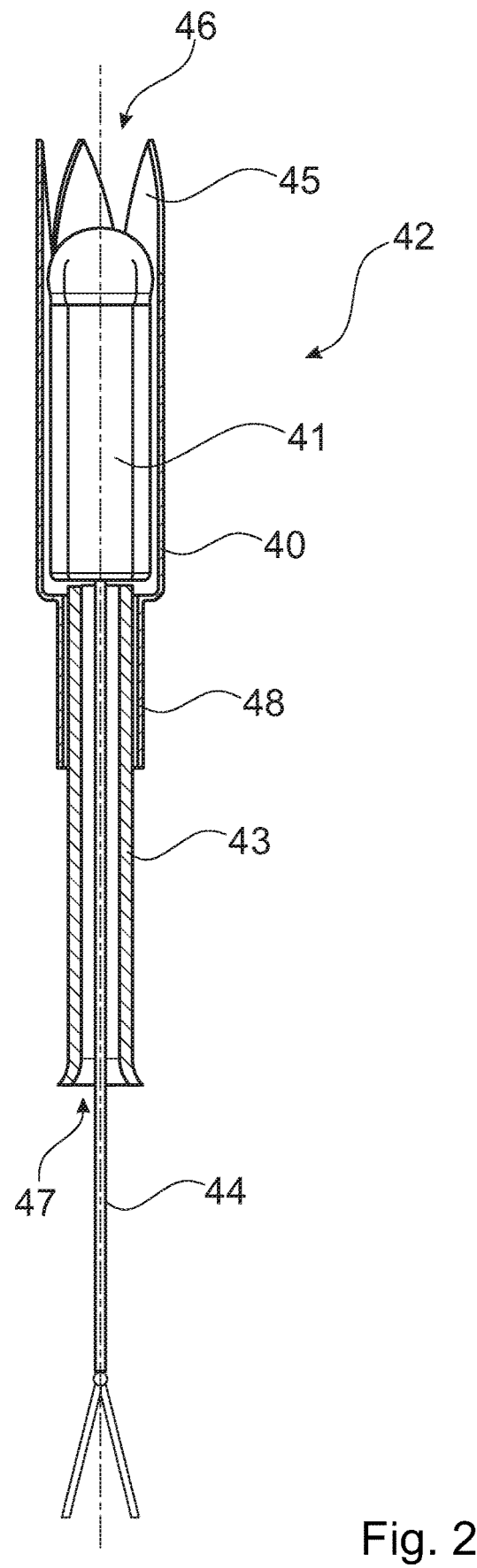
FIG. 2 schematically shows, in longitudinal cross section, an equipped tampon applicator.

FIG. 2 shows an example of an equipped tampon applicator. Here, the equipped tampon applicator 42 is illustrated in original cross section with an inserted tampon 41. The equipped tampon applicator 42 has a distal end 46, which forms the applicator head, and a proximal end 47, which has an opening for a withdrawal thread 44. Said withdrawal thread 44 extends to the inserted tampon 41, which is arranged in a substantially accurately fitting manner in the tampon body 40. Toward the proximal end of the tampon body 40, the tampon applicator tapers into a grip region 48 which is formed integrally with the tampon body 40 and which may selectively also have a rubber lining or roughening or other surface conditioning which facilitates handling. Situated at the distal end 46 is the head opening 45 with a multiplicity of projections formed in the manner of flower petals. In the present example, the equipped tampon applicator 42 is illustrated still in its open form, that is to say prior to the deformation by means of a shaping element 7. During the deformation, the proximal end and the head opening 45 are closed by virtue of the projections being bent inwardly towards the central longitudinal axis of the tampon applicator.

The tampon applicator shown here is to be regarded merely as an example of a tampon applicator suitable for the apparatus according to the invention. Other geometries relating to the head openings, such as a simple cross section, an open head opening (requires no deformation elements) or a head part incised in spiral fashion would likewise be conceivable. It is also possible for multi-part tampon applicators to be provided, in which the head end does not need to be moulded but rather, as a separate cap, is mounted, and for example engaged with latching action, onto the tampon body in a further processing step. Alternative embodiments which involve non-thermoplastic materials, such as for example cardboards or thermosets, may comprise different shaping operations or closure steps in order to close the tampon head.

Figure 3A:
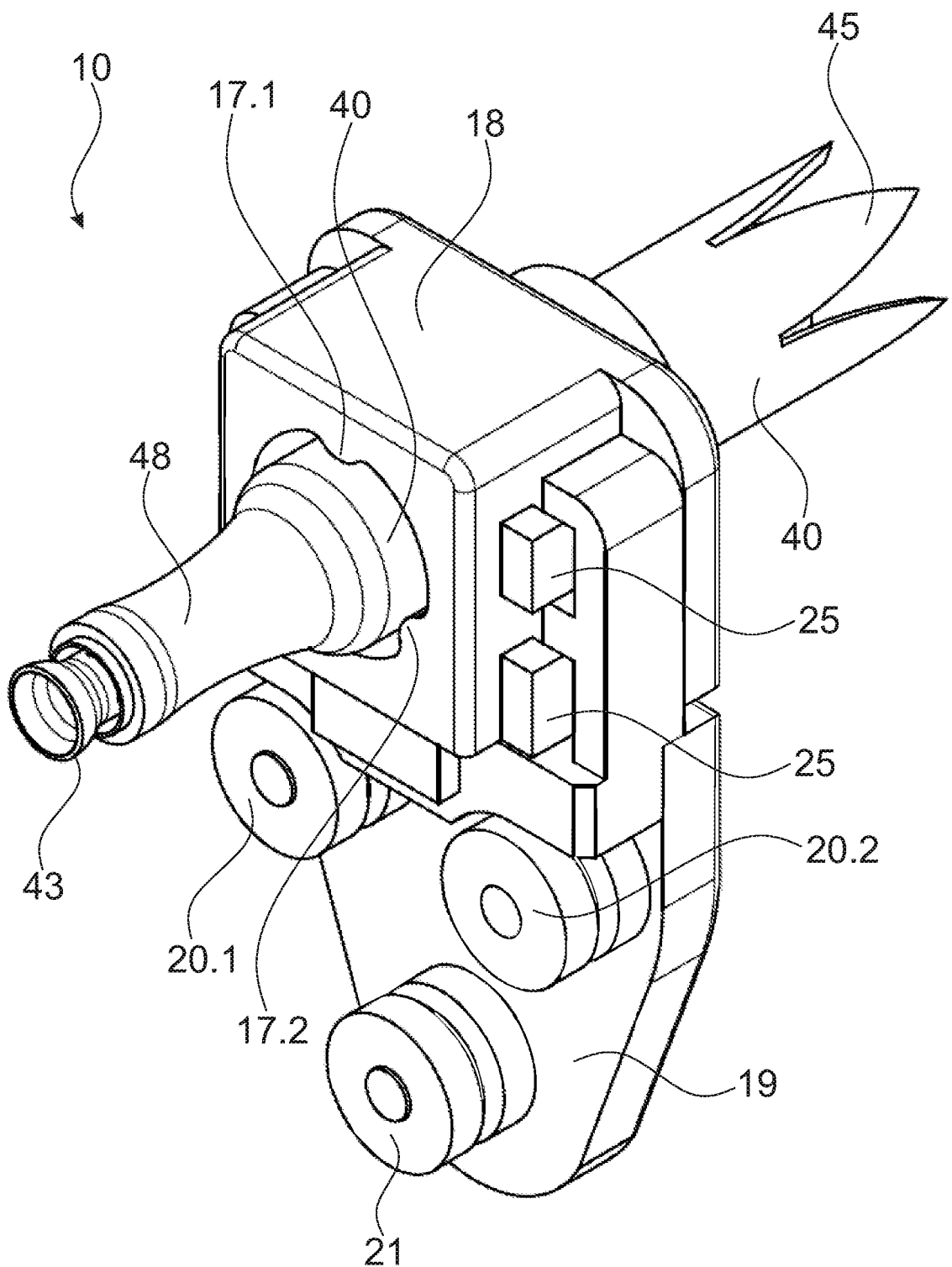
FIG. 3a schematically shows an equipped guide unit.

FIG. 3*a* schematically shows the construction of a guide unit 10 according to the invention. In the present example, the guide unit 10 is shown with a received tampon applicator. The tampon applicator is held on the tampon body 40 by three holding bulges 17.1, 17.2, formed on a holding cassette 18, by means of a positive-fitting and/or force-fitting connection. The holding bulges 17.1, 17.2 extend in straight fashion and into an applicator receptacle of the holding cassette 18 such that the inserted tampon applicator is, at its tampon body 40, compressed to just such an extent that it is securely held without sustaining material damage. The tampon applicator is inserted into the applicator receptacle such that its proximal end with the plunger 43 points toward a front side, and the head end 45 points toward a rear side.

The plunger 43 is not formed as a single piece with the tampon body 40, and is displaceable in a longitudinal direction of the tampon applicator. During the insertion of the tampon and the tampon applicator and the equipping thereof, the plunger 43 is pushed out of the tampon body and assumes the configuration shown in FIG. 2.

The holding cassette 18 is formed as a separate component of the guide unit 10 and is connected by means of latching lugs 25 to a guide element 19. On the guide element 19 there are formed a total of three rollers 20.1, 20.2 and 21. During operation, the rollers 20.1, 20.2, 21 engage into a T-shaped profile of a rail of a guide arrangement, such that the first roller 20.1 and the second roller 20.2 roll on one side, in particular on the outer radius of the guide arrangement, and the counterpart roller 21 rolls on the inner radius of the guide arrangement.

The holding cassette 18 may be mounted so as to be movable with respect to the guide element. For this purpose, the latching lugs 25 are formed such that, below the latching lugs 25, there is a free movement space through which the holding cassette 18 can be displaced with respect to the guide element 19. No spring or similar resetting element is illustrated in this illustration, though may likewise be realized as discussed in the introduction. In the present apparatus, the holding cassette 18 can be easily exchanged. Since the holding cassette 18 can be subject to increased wear as a result of the contact of the tampon applicators, and economic and ecological improvement is furthermore achieved with the present guide unit 10.

Figure 3B:
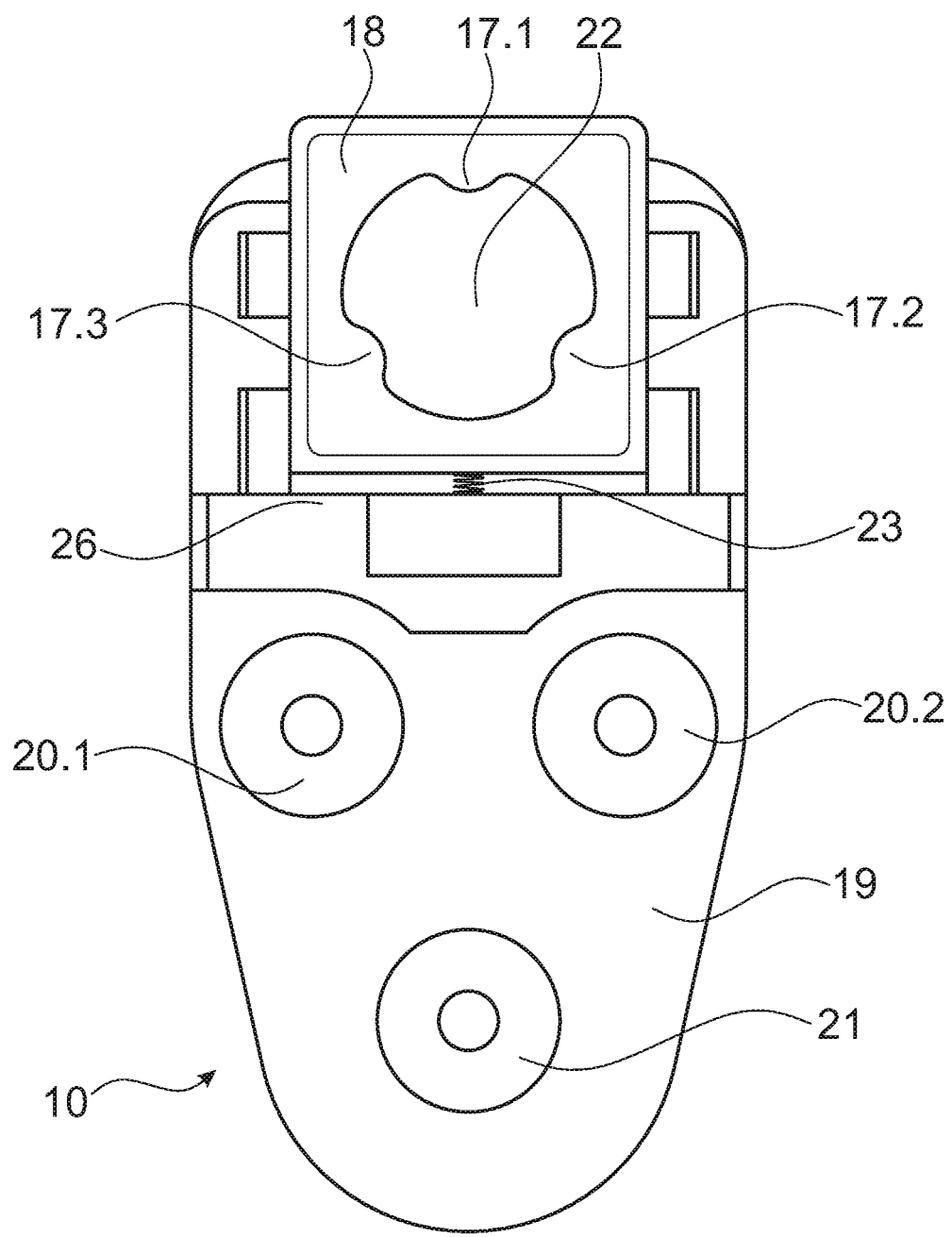
FIG. 3b schematically shows a guide unit in a frontal view.

FIG. 3b shows the guide unit 10 in a plan view. The guide unit 10 is broadly divided into two functional components, the holding cassette 18 and the guide element 19. In the present example, the guide element 19 is equipped with three rollers 20.1, 20.2 and 21, which in the present example are composed of steel and can engage into a corresponding T-shaped profile of a guide arrangement. By means of the three-roller system, the guide element 19 can follow a curved profile of the guide arrangement without spring loading of the rollers 20.1, 20.2 and 21 being necessary. Spring loading may nevertheless self-evidently be implemented.

The holding cassette 18 has an applicator receptacle 22, which is illustrated as a cavity and which extends through the entire thickness of the holding cassette 18 and which is oriented so as to receive a tampon applicator as shown in FIG. 3a. The applicator receptacle has a circular cross section which is indented by three holding bulges 17.1, 17.2, 17.3. It has surprisingly been found that the contact by means of these three holding bulges alone permits optimum hold of the tampon applicator in the guide unit, which is particularly gentle to the applicator material. The holding cassette 18 may be formed as a single piece. Between the holding cassette 18 and the guide element 19, a resetting spring 23 provides a resetting force which compensates a movement of the holding cassette 18 in the frontal plane.

Figure 4:
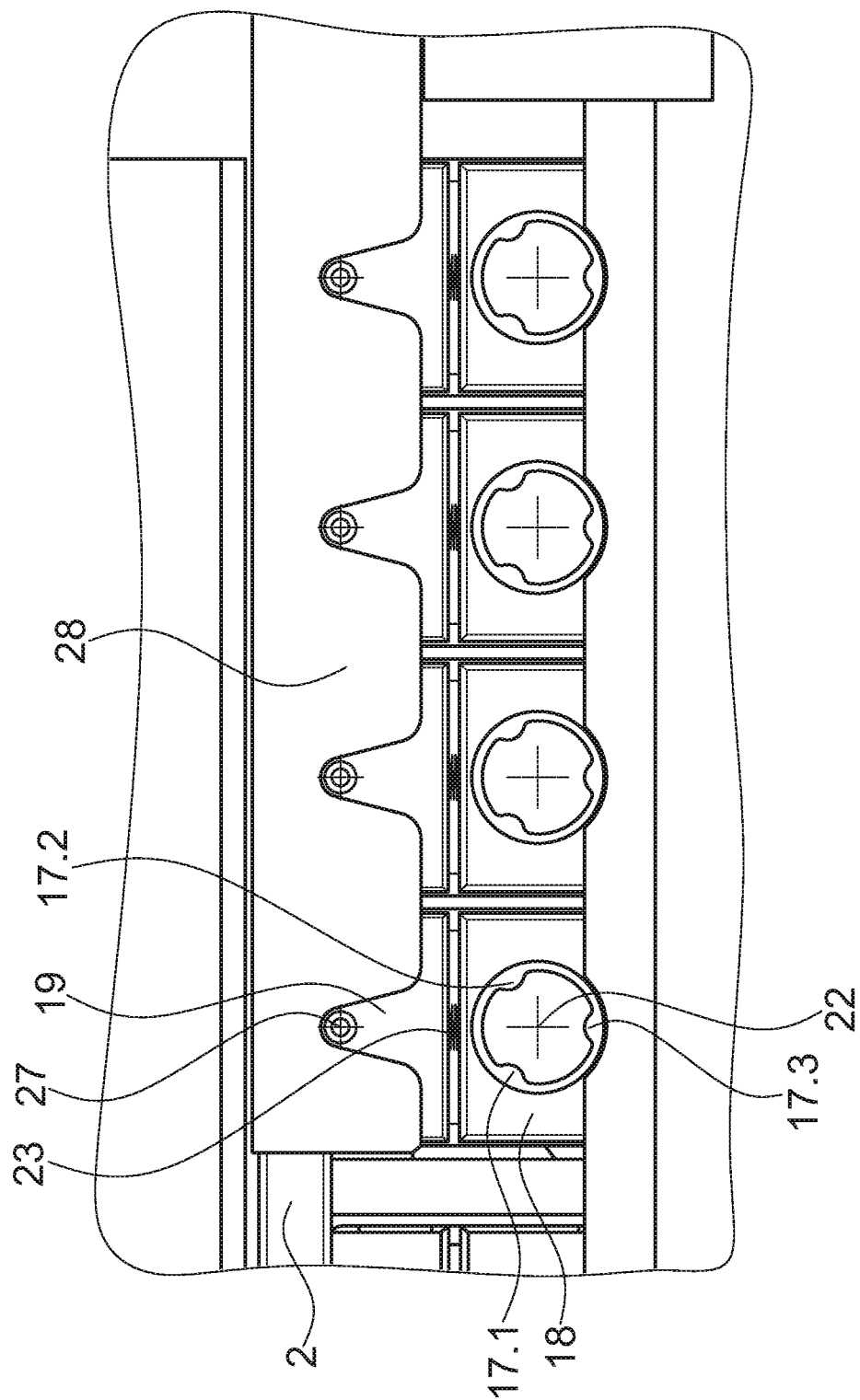
FIG. 4 schematically shows a driver for a batch of guide units.

FIG. 4 illustrates a further aspect of the present invention. The guide units 10 can be individually moved in each case by means of a driver by the drive units in the conveying direction. Alternatively or in addition, a batch of guide units can, by means of a driver 28, be configured with a notched profile which can operatively connect to a pin 27 of in each case one guide unit and in so doing permit an alignment of the guide units and conveyance thereof. In the present illustration, the guide units are, by contrast to FIGS. 3a, 3b, shown from the rear side thereof, but it is likewise possible to see the holding cassette 18 with the three holding bulges 17.1, 17.2 and 17.3. Shown on the opposite side of the pin 27 which is formed on the guide element 19 is the guide arrangement 2, into which the rollers (not shown in this illustration) can engage. This type of driver 28 is suitable for example in processing regions, for example at an entry point, exit point, heating element, shaping element and/or cooling element. In addition to the transport of the guide units, a driver 28 designed in this way can ensure an alignment of the guide units with respect to a processing element.

Figure 5A:
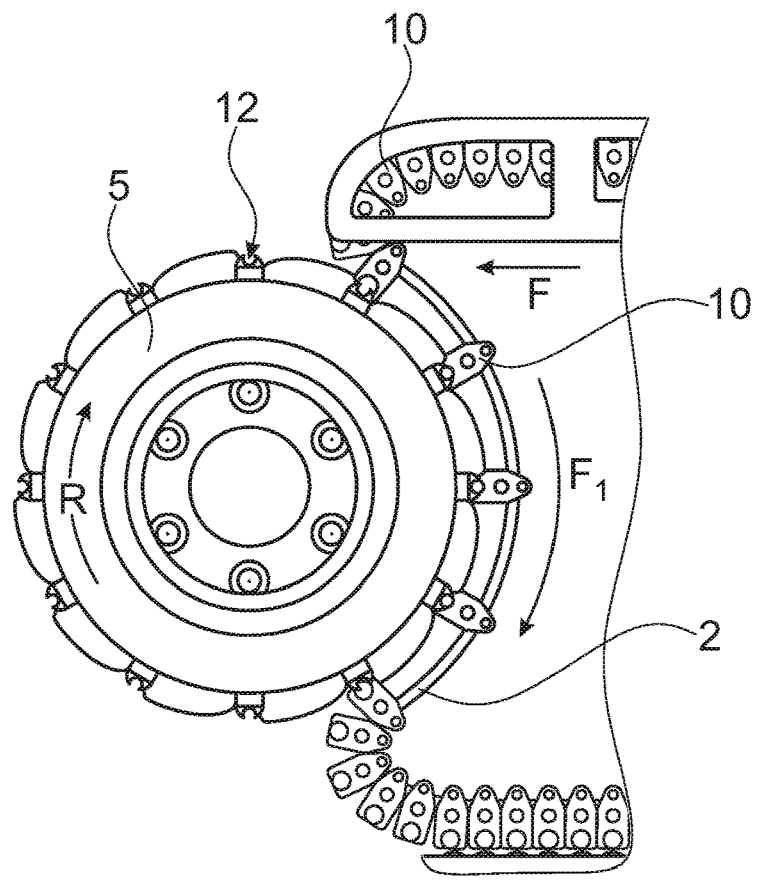
FIG. 5a schematically shows an equipping unit and its associated processing space of a guide arrangement.

FIG. 5a illustrates an embodiment of the processing region of an equipping unit 5. As discussed in the introduction, the equipping unit 5 is formed in the manner of a drum and has radially arranged equipping drivers 12 which, as soon as a guide unit 10 passes into the region of activity as a result of being conveyed in the conveying direction F of the equipping unit 5, can operatively connect to a driving projection 24 and transfer the guide units 10 into the processing radius F1 of the equipping unit 5. During the course of this transport over the processing radius F1, preferably at a time at which the tampon applicator is aligned concentrically with respect to a tampon receptacle of the equipping unit 5, the equipping of the tampon applicator takes place. In the present example, it is also shown how a multiplicity of guide elements can ensure continuous processing and equipping.

Figure 5B:
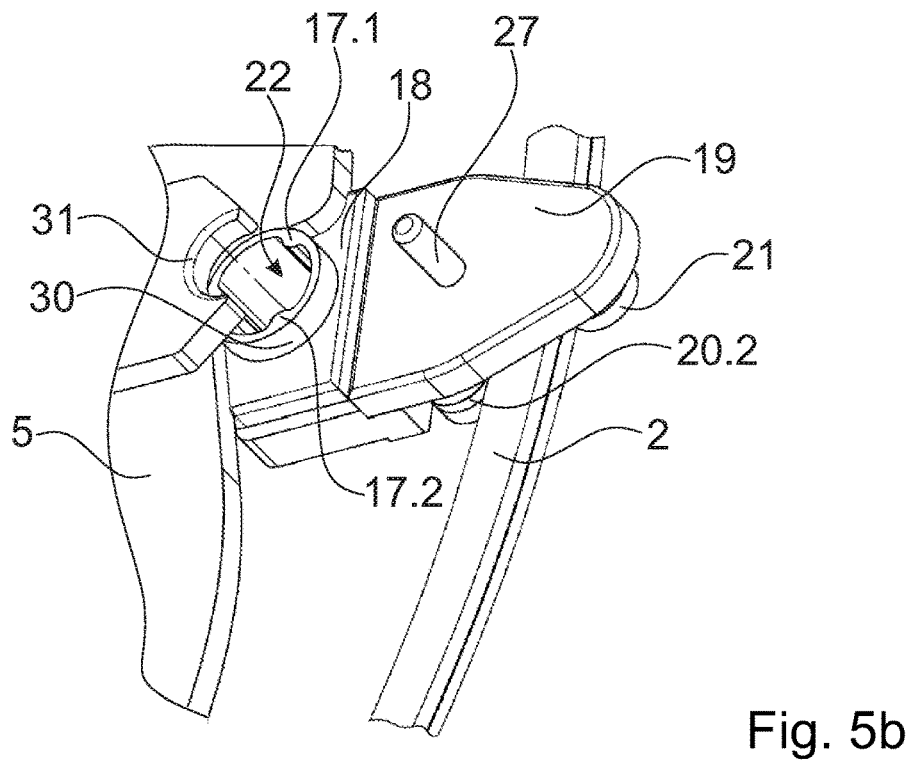
FIG. 5b schematically shows an operative connection between a guide unit and the equipping unit.

FIG. 5b shows a rear view of the equipping radius F1 with a guide unit 10 which has already been engaged by an equipping driver 12. At this point, the guide arrangement 2 describes a radius which substantially follows the circumference of the equipping unit 5. The guide arrangement 2 has a rail into which the rollers 20.2, 21 on the guide element 19 engage. Situated on the rear side of the guide element 19, averted from the rollers, is a pin 27 which is suitable for example for driving the guide unit 10 along by means of the drive elements (not shown in this example) or by means of batch transport by means of the driver (as discussed above). The holding cassette 18 has an applicator receptacle 22 which, by means of three holding bulges 17.1, 17.2, 17.3, hold a tampon applicator. An applicator receptacle aperture 30 is aligned with a tampon guide 31 in this processing space, which, in the case of a concentric arrangement of the longitudinal axes, permits a transfer of the tampon to the tampon applicator. In the present example, the tampon applicator would point with its distal end forward into the plane of the viewer and would be fitted by the equipping unit 5 via the applicator receptacle aperture 30 and the tampon guide 31.

Figure 6A:
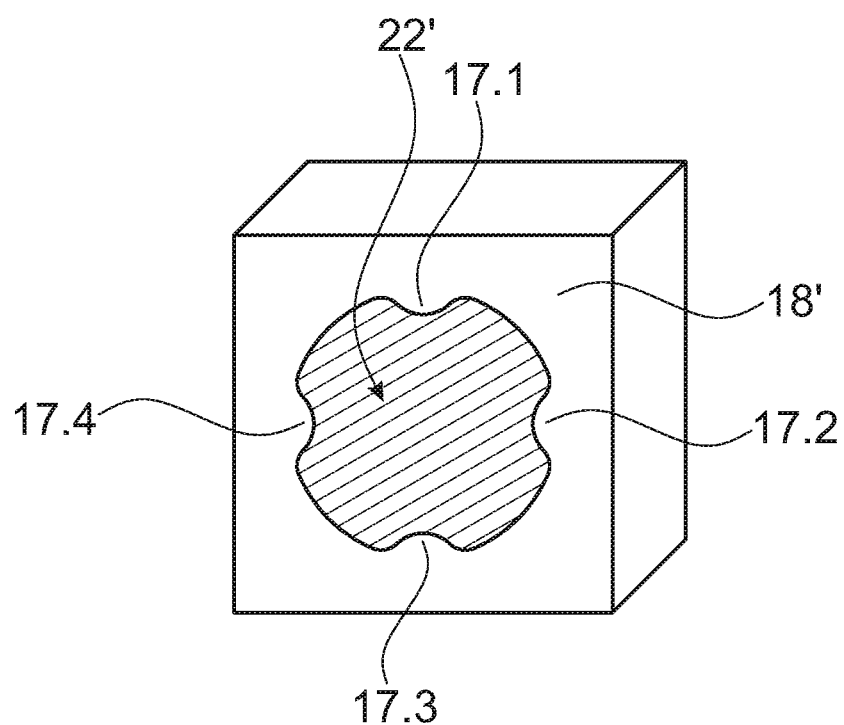
FIG. 6a schematically shows a refinement of a holding cassette.
Figure 6B:
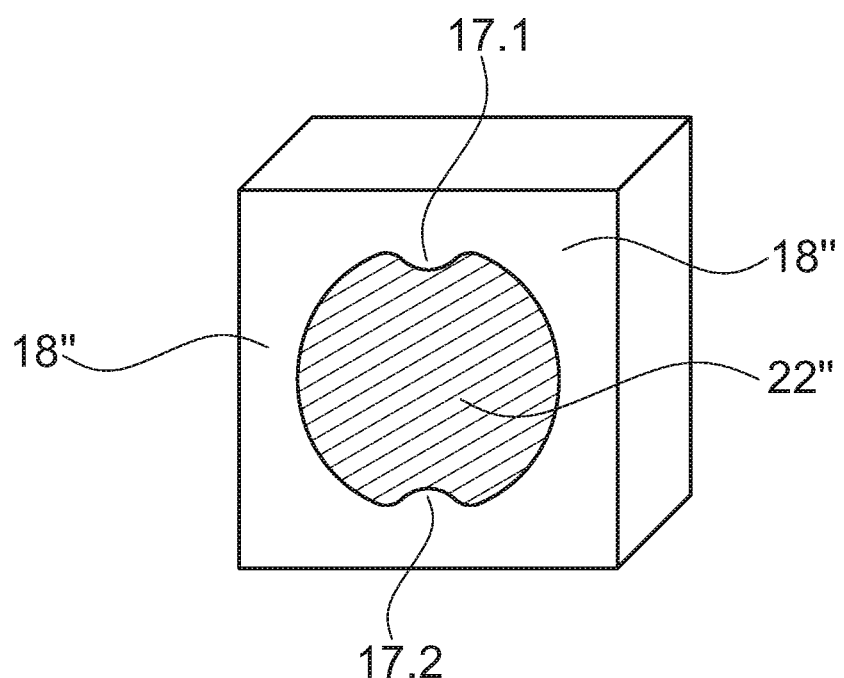
FIG. 6b shows a further schematic refinement of a holding cassette.

FIGS. 6a and 6b show alternative embodiments for the holding cassette 18. FIG. 6a shows a holding cassette 18' in the case of which a recess 22' is delimited by four holding bulges 17.1, 17.2, 17.3 and 17.4. Here, the holding bulges are oriented so as to be arranged substantially symmetrically. This arrangement also enables a tampon applicator to be held in a gentle manner that simultaneously permits reliable processing.

FIG. 6b shows a further alternative embodiment of a holding cassette 18". The holding cassette 18" likewise has an applicator receptacle 22", which in this case is delimited by two holding bulges 17.1, 17.2, which are arranged mirror-symmetrically with respect to one another.

From the exemplary embodiments shown and from the general disclosure, a person skilled in the art will gather further advantageous combinations which are not described in detail here.

With the apparatus according to the invention, the guide unit and the corresponding method, provision is made of a method of said type which is very easy to implement and at the same time permits very high processing rates. Additional advantages are the ease of maintenance and the modularity, which can arrange individual components differently than in the specific example shown here.

LIST OF REFERENCE DESIGNATIONS

1 Apparatus
2 Guide arrangement
3 Entry point
4 Exit point
5 Equipping unit
6 Heating element
7 Shaping element
8 Cooling element
9 Drive element 10 Guide unit
11 Alignment radius
12 Equipping driver
13 Tampon receptacle
14 Limit stop region
15 Separating unit
16 Stopper
17.1 "1st holding bulge"
17.2 "2nd holding bulge"
17.3 "3rd holding bulge"
18 Holding cassette
19 Guide element
20.1 First roller
20.2 Second roller
21 Counterpart roller
22 Applicator receptacle
23 Resetting spring
24 Driving projection
25 Latching lugs
26 Resetting region
27 Pin
28 Driver
29 Buffer region
30 Applicator receptacle aperture
31 Tampon guide
40 Tampon body
41 Tampon
42 Equipped tampon applicator
43 Plunger
44 Withdrawal thread
45 Head opening
46 Distal end
47 Proximal end
48 Grip region
F Conveying direction
F1 Adapted radius
R Direction of rotation

The invention claimed is:

1. An apparatus for equipping tampon applicators with tampons, comprising
   a. an encircling guide arrangement with an entry point, at which the tampon applicators are fed into the apparatus, and with an exit point, at which equipped tampon applicators are discharged;
   b. an equipping unit arranged between the entry point and the exit point and designed for equipping tampon applicators with tampons;
   C. a multiplicity of guide units which are guided on the guide arrangement and which serves for transporting the tampon applicators on the guide arrangement, and wherein the guide units comprise at least one holding cassette with an applicator receptacle and a guide element, wherein the guide element comprises engagement means for the displaceable mounting of the guide unit on the guide arrangement, and the holding cassette is mounted movably with respect to the guide element, and
      wherein the guide units are mounted on the guide arrangement by means of rollers.

2. The apparatus according to claim 1, wherein the guide arrangement comprises at least one processing space with at least one processing unit.

3. The apparatus according to claim 1, wherein each guide unit comprises at least one applicator receptacle for receiving a tampon applicator.

4. The apparatus according to claim 1, wherein the guide units of the multiplicity of guide units are mounted on three rollers of the rollers.

5. The apparatus according to claim 4, wherein a first roller and a second roller are mounted on an outer radius of the guide arrangement, and a counterpart roller is mounted on an inner radius of the guide arrangement.

6. The apparatus according to claim 1, wherein the engagement means are rollers for the displaceable mounting of the guide unit on the guide arrangement.

7. The apparatus according to claim 1, wherein the guide arrangement comprises, along a circuit path, at least one drive element which is designed to convey at least one guide unit in a conveying direction.

8. The apparatus according to claim 1, wherein the equipping unit is constructed in the manner of a drum and comprises a multiplicity of radially arranged equipping drivers, each for driving one driving projection of the guide units.

9. The apparatus according to claim 1, wherein the guide arrangement follows a radius which runs parallel to the radius of rotation of an equipping region of the equipping unit, in a region of the equipping unit.

10. The apparatus according to claim 1, wherein the equipping unit comprises a multiplicity of radially arranged limit stop regions for the coaxial alignment of the applicator receptacle of the guide unit with a tampon receptacle of the equipping unit, such that a tampon can be transferred from the tampon receptacle into the applicator receptacle along a transfer axis.

11. The apparatus according to claim 1, wherein the holding cassette is mounted spring-loaded, with respect to the guide element.

12. The apparatus according to claim 1, wherein each guide unit of the multiplicity of guide units comprises exactly one applicator receptacle for receiving a tampon applicator.

13. A method for equipping tampon applicators with tampons comprising the steps:
   a. providing an apparatus for equipping tampon applicators with tampons, the apparatus comprising:
      i. an encircling guide arrangement with an entry point, at which the tampon applicators are fed into the apparatus, and with an exit point, at which equipped tampon applicators are discharged;
      ii. an equipping unit arranged between the entry point and the exit point and designed for equipping tampon applicators with tampons;
      iii. a multiplicity of guide units which are guided on the guide arrangement and which serves for transporting the tampon applicators on the guide arrangement, and
      wherein the guide units comprise at least one holding cassette with an applicator receptacle and a guide element, wherein the guide element comprises engagement means for the displaceable mounting of the guide unit on the encircling guide arrangement, and the holding cassette is mounted movably with respect to the guide element, and
      wherein the guide units are mounted on the encircling guide arrangement by means of rollers,
   b. providing a guide unit of the multiplicity of guide units for transporting tampon applicators on the encircling guide arrangement;
   c. equipping an applicator receptacle of the at least one holding cassette of the guide unit with a tampon applicator at the entry point;

d. displacing the guide unit on the encircling guide arrangement from the entry point to the equipping unit;

e. equipping the tampon applicator with a tampon; and f. displacing the guide unit on the encircling guide arrangement from the equipping unit to the exit point, and discharging the equipped tampon applicator.

14. The method according to claim 13, wherein, during the equipping of the tampon applicator with a tampon, the applicator receptacle of the guide unit is guided so as to be oriented, with regard to a longitudinal axis of the applicator receptacle, coaxially with respect to a tampon receptacle of the equipping unit.

15. The method according to claim 14, wherein the equipping unit engages by means of at least one equipping driver on a driver projection and guides the guide unit into a transfer position.

\* \* \* \* \*